United States Patent
Lin et al.

(10) Patent No.: US 12,304,892 B2
(45) Date of Patent: May 20, 2025

(54) METHOD FOR PREPARATION OF CARSALAM

(71) Applicant: LONZA GUANGZHOU PHARMACEUTICAL LTD., Guangzhou (CN)

(72) Inventors: Xingbang Lin, Zhongshan (CN); Ji Zhou, Guangzhou (CN)

(73) Assignee: LONZA GUANGZHOU PHARMACEUTICAL LTD., Guangzhou (CN)

( * ) Notice: Subject to any disclaimer, the term of this patent is extended or adjusted under 35 U.S.C. 154(b) by 891 days.

(21) Appl. No.: 17/603,107

(22) PCT Filed: May 18, 2020

(86) PCT No.: PCT/EP2020/063843
§ 371 (c)(1),
(2) Date: Oct. 12, 2021

(87) PCT Pub. No.: WO2020/234245
PCT Pub. Date: Nov. 26, 2020

(65) Prior Publication Data
US 2022/0194906 A1    Jun. 23, 2022

(30) Foreign Application Priority Data

May 20, 2019 (WO) ................ PCT/CN2019/087542
Jun. 14, 2019 (EP) ..................................... 19180140

(51) Int. Cl.
*C07D 265/26* (2006.01)
*C07D 265/20* (2006.01)

(52) U.S. Cl.
CPC .................................. *C07D 265/26* (2013.01)

(58) Field of Classification Search
CPC ............................ C07D 265/26; C07D 265/20
See application file for complete search history.

(56) References Cited

U.S. PATENT DOCUMENTS 3,409,615 A    11/1968    James et al.

FOREIGN PATENT DOCUMENTS

| CN | 104974060 A | * 10/2015 | |
| CN | 108689876 A | * 10/2018 | ........... C07C 231/12 |
| WO | 00/46182 A1 | 8/2000 | |

OTHER PUBLICATIONS

Machine translation Lian (Year: 2025).*
Machine translation Wang (Year: 2025).*
Alina Sen (Authorized Officer), International Search Report and Written Opinion dated Jul. 8, 2020 from International Application No. PCT/EP2020/063843, 7 Pages.
King et al., "Intramolecular Ureido and Amide Group Participation in Reactions of Carbonate Diesters", Journal of the American Chemical Chemical Society, 1992, Vo. 114, No. 27, pp. 10715-10721.

* cited by examiner

*Primary Examiner* — Rayna Rodriguez
*Assistant Examiner* — Elena Vladimirovna Vishnyakova
(74) *Attorney, Agent, or Firm* — MH2 Technology Law Group, LLP

(57) ABSTRACT

The invention discloses a method for preparation of Carsalam by a reaction of salicylamide with diethyl carbonate in the presence of an alkali ethoxide.

16 Claims, No Drawings

METHOD FOR PREPARATION OF CARSALAM

CROSS-REFERENCE TO RELATED APPLICATIONS

This application is a U.S. National Stage application of PCT/EP2020/063843 filed 18 May 2020, which claims priority to International Application No. PCT/CN2019/087542 filed 20 May 2019, and European Patent Application No. 19180140.6 filed 14 Jun. 2019, the entire disclosures of which are hereby incorporated by reference in their entireties.

The invention discloses a method for preparation of Carsalam by a reaction of salicylamide with diethyl carbonate in the presence of an alkali ethoxide.

BACKGROUND OF THE INVENTION

Carsalam is known as an analgesic.

WO 00/46182 A1 discloses in example 1 the preparation of Carsalam from salicylamide with ethyl chloroformate in the solvents pyridine and acetonitrile and with a yield of 85%.

Ethyl chloroformate is a highly toxic chemical whose use is regulated for example in China and poses therefore a risk to the environment, especially to workers during production. Furthermore it is sensitive to moisture and reacts with water which requires respective measures when handling it.

The use of the two solvents pyridine and acetonitrile adds costs to a process, as the solvents must either be discarded in some way or they must be recycled, both again creates costs.

There was a need for a method for preparation of Carsalam with high yield and high purity, but with less disadvantages then the one disclosed in WO 00/46182 A1.

EINHORN ALFRED ET AL "Zur Kenntnis des Carbonylsalicylamide", BERICHTE DER DEUTSCHEN CHEMISCHEN GESELLSCHAFT, WILEY-VCH VERLAG GMBH, vol. 35, (1902), pages 3653-3656, describes the reaction of salicylamide with diphenyl carbonate.

STEPHEN W. KING ET AL: "Intramolecular Ureide and Amide Group Participation in Reactions of Carbonate Diesters", JOURNAL OF THE AMERICAN CHEMICAL SOCIETY, vol. 114, no. 27, (1992), pages 10715-10721, 02 describes the reaction of salicylamide with p-nitrophenyl chloroformate in the presence of pyridine.

A. BOGISCH: "Ueber Carbonylsalicylamid", CHEMIKER-ZEITUNG, CHEMISCHE APPARATUR, vol. 13, no. 66, 1889, page 1078, indicated the preparation of carsalam by the reaction of salicylamide with ethyl chloroformate.

Unexpectedly it was found that the use of diethyl carbonate provides for high yields, high purity, no need of the solvents pyridine or acetonitrile; furthermore diethyl carbonate is not toxic, its use is not regulated as in the case of ethyl chloroformate, and diethyl carbonate is not sensitive to moisture, it does not react with water, all this makes its handling easier and safer for the environment.

Abbreviations

Carsalam Compound of Formula (3)
Salicylamide Compound of Formula (1)

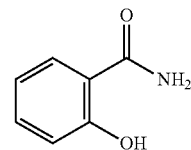

(1)

SUMMARY OF THE INVENTION

Subject of the invention is a method for the preparation of compound of formula (3)

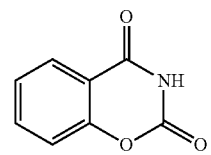

(3)

with two subsequent reactions REAC1 and REAC2;
in the first reaction REAC1 salicylamide is reacted with diethylcarbonate in the presence of an alkali ethoxide to provide compound of formula (3-X)

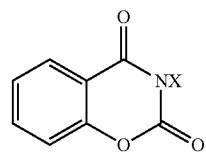

(3-X)

in the second reaction REAC2 compound of formula (3-X) obtained from REAC1 is reacted with a Bronsted acid to provide compound of formula (3);
X is Na or K;
the alkali ethoxide is NaOEt or KOEt.

DETAILED DESCRIPTION OF THE INVENTION

The three substances salicylamide, diethyl carbonate and alkali ethoxide can be mixed for REAC1 in any sequence; preferably, for REAC1 diethyl carbonate and salicylamide are mixed first, then the alkali ethoxide is added to the mixture.

Preferably, the molar amount of alkali ethoxide in REAC1 is from 1 to 2 fold, more preferably from 1 to 1.75 fold, even more preferably from 1 to 1.5 fold, especially from 1.1 to 1.5 fold, more especially from 1.2 to 1.4 fold, of the molar amount of salicylamide.

Preferably, the alkali ethoxide is used in REAC1 in form of a solution in ethanol; more preferably with a concentration of from 10 to 25 wt %, even more preferably of from 15 to 25 wt %, especially of from 18 to 22 wt %, more especially of from 19 to 22 wt %, of ethoxide based on the weight of the solution.

Preferably, the molar amount of diethyl carbonate in REAC1 is from 1 to 5 fold, more preferably from 1 to 4 fold, even more preferably from 2 to 4 fold, especially from 2.5 to 3.5 fold, of the molar amount of salicylamide.

Preferably, REAC1 is done at a reaction temperature TEMP1 of from 20 to 160° C., more preferably of from 40 to 140° C., even more preferably of from 60 to 120° C., especially of from 60 to 100° C., more especially of from 70 to 90° C., even more especially of from 75 to 85° C.

Preferably, the reaction time TIME1 of REAC1 is from 30 min to 8 h, more preferably of from 1 to 6 h, even more preferably of from 1 to 4 h, especially of from 1 to 3 h, more especially of from 1.5 to 2.5 h.

REAC1 can be done at ambient pressure or at elevated pressure, preferably the pressure is adjusted in such a way that the desired reaction temperature can be set in view of the vapor pressure of the reaction mixture.

Preferably, the alkali ethoxide is NaOEt and X is Na.

Preferably, the molar amount of the Bronsted acid in REAC2 is from 1 to 2 fold, more preferably from 1.01 to 1.8 fold, even more preferably from 1.05 to 1.6 fold, especially from 1.05 to 1.4 fold, more especially from 1.1 to 1.2 fold, of the molar amount of alkali ethoxide.

The Bronsted acid protonates compound of formula (3-X), therefore the pKa of the Bronsted acid is lower than the pKa of compound of formula (3-X).

Preferably, the Bronsted acid is selected from the group consisting of HCl, $H_2SO_4$, $HNO_3$, $HClO_4$, HBr and $H_3PO_4$;
more preferably the Bronsted acid is selected from the group consisting of HCl, $H_2SO_4$, and $H_3PO_4$;
even more preferably the Bronsted acid is HCl.

The Bronsted acid preferably used in form of an aqueous solution.

In case of the Bronsted acid being HCl, the HCl is preferably used in form of an aqueous solution with a concentration of from 3 to 12.6 M, more preferably of from 5 to 12.6 M, even more preferably of from 7 to 12.6 M, especially of from 9 to 12.6 M, more especially of from 11 to 12.6 M; even more especially of from 11.5 to 12.6 M. In one embodiment, the HCL is HCl conc. In another embodiment, the HCl is used in form of an aqueous solution with a concentration of 12 M.

Another way to characterize the HCl which can be used in form of an aqueous solution is the concentration in wt % of HCl based on the total weight of the aqueous HCl solution, such as from 10 to about 38 wt %, from 16 to about 38 wt %, from 22 to about 38 wt %, from 28 to 38 wt %, 33 to 38 wt %.

The skilled person is aware of the concentrations of aqueous HCl available on the market; even the highest concentration available on the market may be used in REAC2.

For REAC2, compound of formula (3-X) and the Bronsted acid can be mixed in any way, preferably, the Bronsted acid is added to compound of formula (3-X), more preferably, the Bronsted acid is added to the reaction mixture from REAC1 containing compound of formula (3-X).

Preferably, REAC2 is done at a reaction temperature TEMP2 of from 20 to 100° C., more preferably of from 30 to 100° C., even more preferably of from 30 to 90° C., especially of from 30 to 80° C., more especially of from 30 to 70° C., even more especially of from 30 to 60° C., in particular of from 40 to 60° C., more in particular of from 45 to 55° C.

Preferably, the reaction time TIME2 of REAC2 is from 0.5 to 4 h, more preferably of from 0.5 to 2 h, even more preferably of from 0.5 to 1.5 h.

REAC2 can be done at ambient pressure or at elevated pressure, preferably the pressure is adjusted in such a way that the desired reaction temperature can be set in view of the vapor pressure of the reaction mixture.

Between REAC1 and REAC2, the reaction mixture obtained from REAC1 can be mixed with water;
the amount of water can be from 0.1 to 1.5 fold, preferably from 0.3 to 1.2 fold, more preferably from 0.3 to 0.9 fold, even more preferably from 0.4 to 0.8 fold, especially from 0.5 to 0.7 fold, of the combined weights of salicylamide, diethyl carbonate and alkali ethoxide.

Preferably, the addition of water is done at TEMP2.

Preferably, the water is added to the reaction mixture obtained from REAC1.

Preferably, after REAC2 the reaction mixture is cooled in a cooling COOL3 to a temperature TEMP3 of from −20 to 10° C., more preferably of from −10 to 5° C., even more preferably of from −5 to 5° C., in particular to 0° C.

COOL3 is done before an isolation of compound of formula (3) from the reaction mixture obtained from REAC2.

Compound of formula (3) may be isolated after REAC2 or after a COOL3 by standard methods known to the skilled person, such as filtration and subsequent drying. The filter cake obtained by filtration may be washed by ethanol, water or by both; any drying may be done under vacuum and/or elevated temperature, such as vacuum and at a temperature of from 40 to 60° C.

In one embodiment, the method comprises
REAC1,
REAC2, and
COOL3;
preferably the method comprises
REAC1,
the mixing of the reaction mixture obtained from REAC1 with water
REAC2, and
COOL3.

Preferably, compound of formula (3-X) is not isolated between REAC1 and a mixing of the reaction mixture obtained from REAC1 with water.

Preferably, compound of formula (3-X) is not isolated between a mixing of the reaction mixture obtained from REAC1 with water and REAC2.

Preferably, compound of formula (3-X) is not isolated between REAC1 and REAC2.

Preferably, compound of formula (3) is not isolated between REAC2 and a COOL3.

Preferably, there is no isolation of compound of formula (3-X) and no isolation of compound of formula (3) between REAC1 and a COOL3.

Preferably, REAC1, REAC2, a mixing of the reaction mixture obtained from REAC1 with water and a COOL3 are done in one and the same reaction vessel without transfer of any reaction mixture from this reaction vessel to any other reaction vessel and without any intermediate isolation of compound of formula (3-X) and with isolation of compound of formula (3) only after REAC2 or only after a COOL3, if a COOL3 is done.

Preferably, the reaction mixture after REAC1 is a suspension of the alkali salt of Carsalam.

Preferably, the reaction mixture after a mixing of the reaction mixture obtained from REAC1 with water is a solution of the alkali salt of Carsalam.

Preferably, the reaction mixture after REAC2 is a suspension of Carsalam.

Preferably, the reaction mixture after a COOL3 is a suspension of Carsalam.

EXAMPLES

Abbreviations eq. equivalent, eq, molar equivalent if not stated otherwise

Materials

| | |
|---|---|
| Diethyl carbonate | Acros (Thermo Fisher Scientific), 99% |
| Salicylamide | Macklin Inc., Shanghai, China, 99% |

Analytical Methods
HPLC Method for Determining the Purity of Carsalam
Instrumental Parameters

| | |
|---|---|
| Instrument | Waters Arc_2489 or equivalent |
| Column | YMC basic, 250 * 4.6 mm * 3 micro meter or equivalent |
| Flow | 0.8 mL/min |
| Injection volume | 5 microL |
| Needle wash | Acetonitrile |
| Column temperature | 25° C. |
| Sample temperature | 4° C. |
| Wavelength | 230 nm |
| Run Time | 40 min |
| 10M potassium hydroxide solution | Weigh 5.6 ± 0.5 g potassium hydroxide in a flask, then add 10 mL pure water in it, stir the solution until the solid dissolved completely, place it at room temperature until it cool down. |
| Eluent A | 20 mM $KH_2PO_4$ pH 6.8 e.g. Dissolve 2.72 ± 0.2 g $KH_2PO_4$ in 1000 mL water, adjust pH to 6.8 with 10M potassium hydroxide solution |
| Eluent B | Acetonitrile |

| Gradient | T(min) | A(%) | B(%) |
|---|---|---|---|
| | 0.0 | 90 | 10 |
| | 5.0 | 80 | 20 |
| | 15.0 | 75 | 25 |
| | 25.0 | 30 | 70 |
| | 30.0 | 30 | 70 |
| | 30.1 | 90 | 10 |
| | 40.0 | 90 | 10 |

Blank: Acetonitrile/water (1/1, v/v)
Sample Solution

| | |
|---|---|
| Sample | 24.0 ± 2.0 mg Add into a 50 mL of volumetric flask, add blank to dissolve, solubilize, dilute to the mark with blank, mix well. |

Stability: solution is stable for 2 days under 4° C.

Specified impurity and each single unspecified impurity $$Single\,impurity_X\ [\%\ \text{area}] = \frac{\text{peak }area_X}{\text{peak }area_{total}} \times 100\%$$

peak area$_X$: area of individual peak in the sample solution
peak area$_{total}$: total area of all peaks in the sample solution
Carsalam Purity
Calculate the purity of Carsalam by subtracting the sum of impurities from 100
Carsalam % area = 100 - sum of impurities (in % area)
Remark: peaks ≥ 0.05 % area will be integrated.
A peak, whose peak area in the chromatogram of a sample is a maximum of 1.5 times the area of a corresponding interfering peak in the blank chromatogram, is not integrated.
Report the area % of specified impurities, any single unspecified impurity and the purity of Carsalam.
Reporting limit 0.05 % area.

Example 1

To a 1.5 L reactor, 253 g diethyl carbonate (2.15 mol, 3.0 eq.) and 100 g salicylamide (0.715 mol, 1.0 eq.) were charged. The mixture was a suspension and was stirred for 15 min. Then 309 g 20 wt % EtONa/EtOH (0.93 mol, 1.3 eq.) were charged to the reactor. The reaction mixture become a clear solution. The reaction mixture was heated to 80° C. and stirred at 80° C. for 2 h. A white precipitate was observed. The reaction mixture was cooled to 50° C. 387 g water were added and the reaction mixture was stirred for about 15 min until it became a clear solution. 109 g 12 M HCl (1.07 mol, 1.5 eq.) were then added dropwise to the reactor in 1 h, a precipitate formed when the 12 M HCl was charged. The reaction mixture was cooled to 0° C. in 2 h. The suspension was filtered providing a filter cake. 231 g ethanol were added to the reactor and stirred for 15 min, and the filter cake was washed with this ethanol from the reactor. Then the cake was washed with 515 g water and 231 g ethanol, the cake was dried under vacuum (10 kPa) at 50° C. for 5 h. 107 g Carsalam as a white crystalline product were obtained.

Yield 90%
HPLC purity>99.9%.
$^1$H NMR (400 MHz, DMSO) delta 7.95 (dd, J=8.0, 1.4 Hz, 1H), 7.80 (td, J=8.1, 1.7 Hz, 1H), 7.46-7.36 (m, 2H).

The invention claimed is:
1. A method for the preparation of compound of formula (3)

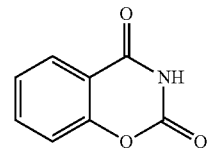

(3)

with two subsequent reactions REAC1 and REAC2;
in the first reaction REAC1 salicylamide is reacted with diethylcarbonate in the presence of an alkali ethoxide to provide compound of formula (3-X)

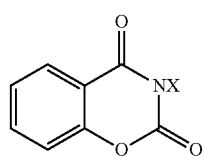

(3-X)

in the second reaction REAC2 compound of formula (3-X) obtained from REAC1 is reacted with a Bronsted acid to provide compound of formula (3);

X is Na or K;

the alkali ethoxide is NaOEt or KOEt.

2. Method according to claim 1, wherein for REAC1 diethyl carbonate and salicylamide are mixed first, then the alkali ethoxide is added to the mixture.

3. Method according to claim 1, wherein the molar amount of alkali ethoxide in REAC1 is from 1 to 2 fold of the molar amount of salicylamide.

4. Method according to claim 1, wherein the molar amount of diethyl carbonate in REAC1 is from 1 to 5 fold of the molar amount of salicylamide.

5. Method according to claim 1, wherein the alkali ethoxide is NaOEt and X is Na.

6. Method according to claim 1, wherein the molar amount of the Bronsted acid in REAC2 is from 1 to 2 fold of the molar amount of alkali ethoxide.

7. Method according to claim 1, wherein the pKa of the Bronsted acid is lower than the pKa of compound of formula (3-X).

8. Method according to claim 1, wherein the Bronsted acid is selected from the group consisting of HCl, $H_2SO_4$, $HNO_3$, $HClO_4$, HBr and $H_3PO_4$.

9. Method according to claim 1, wherein the Bronsted acid preferably used in form of an aqueous solution.

10. Method according to claim 1, wherein for REAC2, the Bronsted acid is added to compound of formula (3-X).

11. Method according to claim 1, wherein between REAC1 and REAC2, the reaction mixture obtained from REAC1 is mixed with water.

12. Method according to claim 11, wherein the amount of water is from 0.1 to 1.5 fold of the combined weights of salicylamide, diethyl carbonate and alkali ethoxide.

13. Method according to claim 11, wherein the water is added to the reaction mixture obtained from REAC1.

14. Method according to claim 1, wherein after REAC2 the reaction mixture is cooled in a cooling COOL3 to a temperature TEMP3 of from −20 to 10° C. before an isolation of compound of formula (3) from the reaction mixture obtained from REAC2.

15. Method according to claim 1, wherein compound of formula (3-X) is not isolated between REAC1 and REAC2.

16. Method according to claim 14, wherein compound of formula (3) is not isolated between REAC2 and COOL3.

* * * * *